United States Patent
Gibbs

(10) Patent No.: US 6,620,146 B2
(45) Date of Patent: Sep. 16, 2003

(54) ADULT INCONTINENCE ARTICLE WITH BODY-SHAPING ELASTICS

(75) Inventor: Bernadette Mary Gibbs, Statham, GA (US)

(73) Assignee: Paragon Trade Brands, Inc., Norcross, GA (US)

(*) Notice: Subject to any disclaimer, the term of this patent is extended or adjusted under 35 U.S.C. 154(b) by 0 days.

(21) Appl. No.: 09/838,251

(22) Filed: Apr. 20, 2001

(65) Prior Publication Data

US 2003/0139726 A1 Jul. 24, 2003

(51) Int. Cl.[7] ............................................. A61F 13/15
(52) U.S. Cl. ................................... 604/385.3; 604/392
(58) Field of Search ................... 604/385.24–385.3, 604/392, 396

(56) References Cited

U.S. PATENT DOCUMENTS

| | | | | |
|---|---|---|---|---|
| 5,415,649 A | * | 5/1995 | Watanabe et al. | 604/385.29 |
| 5,735,839 A | * | 4/1998 | Kawaguchi et al. | 604/385.29 |
| 5,749,865 A | * | 5/1998 | Yamamoto et al. | 604/385.29 |
| 5,807,371 A | * | 9/1998 | Toyoda et al. | 428/343 |
| 5,817,087 A | * | 10/1998 | Takabayashi et al. | 604/385.29 |
| 5,853,405 A | * | 12/1998 | Suprise | 604/385.29 |
| 5,858,012 A | * | 1/1999 | Yamaki et al. | 604/358 |
| 5,876,392 A | * | 3/1999 | Hisada | 604/385.29 |
| 5,941,865 A | * | 8/1999 | Otsubo et al. | 604/378 |
| 6,149,637 A | * | 11/2000 | Allen et al. | 604/366 |
| 6,210,386 B1 | * | 4/2001 | Inoue | 604/385.01 |
| 6,264,643 B1 | * | 7/2001 | Toyoda | 604/385.29 |
| 6,306,122 B1 | * | 10/2001 | Narawa et al. | 604/385.3 |
| 6,364,863 B1 | * | 4/2002 | Yamamoto et al. | 604/385.27 |
| 6,369,291 B1 | * | 4/2002 | Uchimoto et al. | 604/367 |
| 6,375,646 B1 | * | 4/2002 | Widlund et al. | 604/385.3 |

* cited by examiner

Primary Examiner—Weilun Lo
Assistant Examiner—Jamisue A. Webb
(74) Attorney, Agent, or Firm—Hunton & Williams

(57) ABSTRACT

The garment of the present invention has a waist region for fitting around a wearer's waist and a crotch region that extends between the wearer's legs. Shaping elastics are attached to the garment in one or more regions to cause the wearer's body to take on a more desirable shape, and may improve the comfort of the garment. Thus equipped, the garment may also provide physically therapeutic benefits to a wearer.

14 Claims, 5 Drawing Sheets

Fig. I

ADULT INCONTINENCE ARTICLE WITH BODY-SHAPING ELASTICS

FIELD OF THE INVENTION

The present invention relates generally to absorbent garments. Particularly, the invention relates to adult incontinence garments having additional layers of elastics to provide body shaping, improve comfort and fit, and provide other benefits.

BACKGROUND OF THE INVENTION

Adult incontinence products generally are pant-like garments that are intended to contain body exudates released by the wearer. A waist portion wraps around a wearer's torso to hold the garment in place, and a crotch portion of the garment extends from the waist between the wearer's legs. Such garments are conventionally made with elastics or other fitting devices in the waist portion to fit the garment to the wearer to prevent leakage and to hold the garment onto the wearer. The garment also may have elastics located in the proximity of the leg openings to prevent body exudates from escaping out of the garment around the wearer's legs.

Adult incontinence products may have a one piece construction, in which case a garment may be manufactured from a single assembly of parts joined to itself to form a garment. Such products also may have multi-piece construction in which the garment is made from several subassemblies that may be joined, for instance, to form a garment having seams at the crotch and sides. These garments are traditionally donned by being pulled up a user's legs, but they may also be equipped with open seams that are releasably closable to assist with donning the garment.

People often desire to appear slimmer, firmer, or more shapely than they would normally appear. There have been many attempts to provide body-shaping undergarments that provide a person with a more desirable body shape, such a slimmer or more shapely appearance. For example, U.S. Pat. No. 5,954,564, issued to Ganz, which is incorporated herein by reference in its entirety and in a manner consistent with the present invention, discloses underwear having elastic buttock supporting panels that provide support to the wearer's buttocks to provide a slimmer, firmer appearance. U.S. Pat. No. 5,390,999, issued to Lawson et al., the disclosure of which is incorporated herein by reference in its entirety, also provides a body-shaping garment in the form of pantyhose.

A fallback of these garments is that they do not provide absorbency features available in an adult incontinence garment. Furthermore, it would be difficult to use an adult incontinence garment in conjunction with a conventional body shaping garment.

Conventional adult incontinence garments do not provide body-shaping benefits. For example, elastics that are placed in the waists of conventional adult incontinence garments often comprise a number of thin elastic bands or strands. These bands are typically adhesively bonded to one or more of the sheets that comprise the garment such that when the elastics contract, the garment is held on the wearer and leakage is inhibited. Such elastics are typically relatively weak so that they can easily stretch to comfortably fit around the wearer's body. Such elastics may provide little, if any, support and body shaping to the wearer. Other problems also exist.

SUMMARY OF THE INVENTION

The present invention overcomes the drawbacks of the prior art by providing an adult incontinence garment ("garment") that provides body-shaping features. The features of the invention may be achieved by providing a garment comprising body-shaping elastics. The body-shaping elastics provide elastically stiffer regions of the garment that force the wearer's body to assume a more desirable shape or appearance and may provide other benefits.

The garment generally comprises a substantially liquid-impervious outer layer attached directly or indirectly to a substantially liquid-pervious inner layer to form a garment having a waist hole and a pair of leg holes. A waist edge defines the outer perimeter of the waist hole, and a waist region proximal to the waist edge encircles a wearer's waist. A crotch region is located between the leg holes, and extends between the wearer's legs. An absorbent layer is disposed between the inner and outer layers in at least part of the crotch region and is attached to the garment either directly or indirectly. One or more shaping elastics preferably are operatively associated with at least one of the inner and outer layers of the garment. The shaping elastics cause the body of the wearer to assume a more desirable shape, and may provide other benefits.

In a demonstrative construction of the invention, the shaping elastics are located to support or shape the wearer's hips. In other demonstrative constructions of the invention, the shaping elastics are located to support or shape the wearer's back or stomach. In another demonstrative construction, the shaping elastics are located to support at least one of the wearer's back, hips, and stomach.

In another demonstrative construction, the shaping elastics are located on a skirt-like portion of the garment which may be pulled down around the wearer's thighs or up around the wearer's waist.

DETAILED DESCRIPTION OF THE PREFERRED EMBODIMENTS

Figure 1:
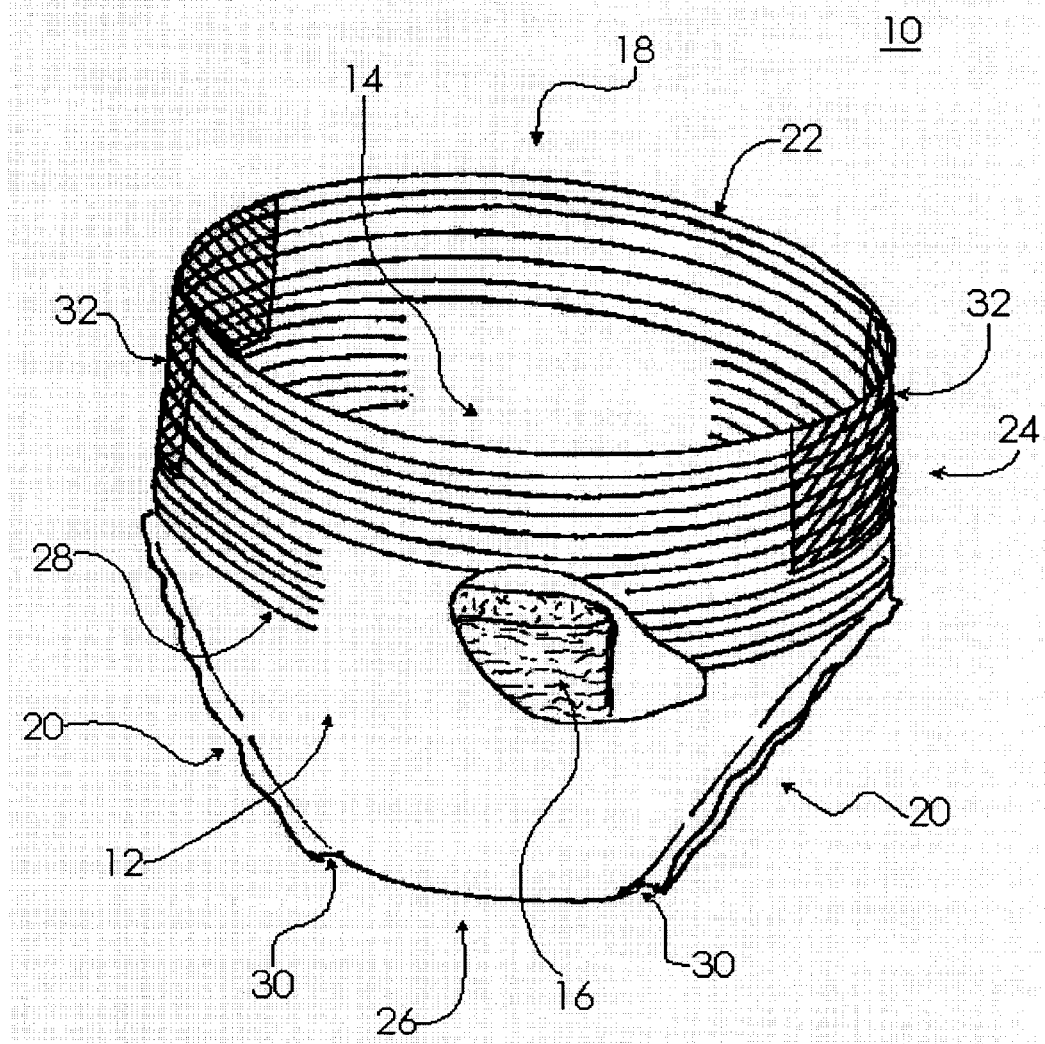
FIG. 1 is a partially cut-away view of an embodiment of the present invention, with shaping elastics disposed in the hip portions of the waist region.

As used herein, the terms "absorbent garment," "absorbent article," "article," and "garment" refer to garments that absorb and contain exudates. More specifically, these terms refer to garments that are placed against or in proximity to the body of the wearer to absorb and contain various exudates discharged from the body. A non-exhaustive list of examples of absorbent garments includes diapers, diaper covers, disposable diapers, training pants, feminine hygiene products and adult incontinence products. The term "disposable absorbent garment" refers to absorbent garments that are intended to be discarded or partially discarded after a single use (i.e., they are not intended to be laundered or otherwise restored or reused). Such garments may have a unitary construction or may be made from several subassemblies. In addition, such garments may have permanent seams, in which case the garment is pulled up the wearer's legs and on to the wearer. Such garments may also have releasable seams, which may be opened to facilitate donning of the garment, then securely closed to hold the garment on the wearer.

For simplicity, the preferred embodiments of the present invention will be described in terms of an adult incontinence garment with permanent seams. It should be understood, however, that the absorbent garment of the preferred embodiments can be used with all of the foregoing classes of absorbent garments, without limitation, whether disposable or otherwise. These classifications are used interchangeably throughout the specification, but are not intended to limit the claimed invention. The invention will be understood to encompass, without limitation, all classes and types of absorbent garments, including those described above.

In general terms, the garment of an embodiment of the present invention comprises an inward-facing substantially liquid-pervious topsheet overlying an outward-facing substantially liquid-impervious backsheet. The topsheet, backsheet, or both are shaped to have a waist hole and two leg holes. A waist region wraps around the wearer's waist, and a crotch region extends between the wearer's legs. Conventional fitting elastics may be attached to at least one of the topsheet and backsheet in the waist region. Conventional fitting elastics conform to the shape of the wearer, and usually are used to hold the garment on the wearer and prevent leakage. The features and uses of fitting elastics are described in U.S. Pat. No. 5,575,783, issued to Clear et al., which is incorporated herein by reference in its entirety and in a manner consistent with the present invention. The garment may also be equipped with other devices or structures to hold the garment on the wearer. Shaping elastics preferably are attached to the garment in one or more target regions to stiffen the garment in the target regions. The shaping elastics are generally stiffer than conventional fitting elastics, and cause the body of the wearer to assume a more desirable shape in the target region, and may provide other benefits.

The garment further comprises an absorbent core for absorbing and storing body exudates. The absorbent core preferably is disposed between the topsheet and the backsheet in the crotch region, and may extend into the waist region. At least part of the interior-facing topsheet is liquid-pervious to allow fluids to be absorbed into the absorbent core. The exterior-facing backsheet is generally liquid-impervious to prevent the fluid in the absorbent core from being released from the garment, and onto or into the garment, but may be partly or wholly gas-pervious to provide the garment with breathability to enhance user comfort. An outer cover may also be placed on the liquid-impervious surface to improve the tactile feel or comfort of the garment.

These and other features, functions, and uses of the present invention are described in greater detail herein. For clarity, features that appear in more than one Figure have the same reference number in each Figure.

FIG. 1 is a partially cut away view of a preferred embodiment of the present invention. Those skilled in the art will appreciate that the embodiments of the invention will be useful with absorbent garments other than the preferred "pull-on" garments shown in the Figures. The garment 10 comprises a backsheet 12 overlaid by a topsheet 14, and an absorbent core 16 disposed between the backsheet 12 and topsheet 14. The various parts of the garment 10 are assembled to provide a waist hole 18 and a pair of leg holes 20. The perimeter of the waist hole 18 is defined by the waist edge 22 of the garment 10, and a waist region 24 is proximal to the waist edge 22. In use, the waist region 24 wraps around the wearer's torso. A crotch region 26 is located between the leg holes 20. The crotch region 26 preferably extends between the wearer's legs in use.

The absorbent core 16 may be made from any suitable material or materials known in the art. The invention is not intended to be limited to any specific materials for these components. In a preferred embodiment, the absorbent core 16 comprises a super absorbent polymer distributed within a fibrous structure. Absorbent cores of this type are known in the art, and exemplary absorbent cores are described in U.S. Pat. No. 5,281,207, issued to Chmielewski et al., and U.S. Pat. No. 5,863,288, issued to Baker, which are herein incorporated by reference in their entirety. The absorbent core 16 may also have one or more transfer layers or acquisition layers for assisting the core in handling fluid surges, preventing rewet, or other purposes. Those skilled in the art are capable of selecting materials, dimensions, and locations for absorbent cores useful in the invention.

The topsheet 14 and backsheet 12 may be constructed from a wide variety of materials known in the art. The invention is not intended to be limited to any specific materials used to manufacture these components. The topsheet 14 and backsheet 12 preferably are shaped and sized according to the requirements of each of the various types of absorbent garments or to accommodate various user sizes.

The backsheet 12 generally comprises any suitable pliable substantially liquid-impervious material known in the art or later discovered. Typical backsheet materials include films of polyethylene, polypropylene, polyester, nylon, polyvinyl chloride, and blends of these materials. For example, the backsheet 12 can be made of a pigmented polyethylene film having a thickness in the range of 0.02–0.04 mm. In addition, the backsheet 12 may be covered with a fibrous, nonwoven fabric (not shown) such as is disclosed, for example, in U.S. Pat. No. 4,646,362 issued to Heran et al., which is hereby incorporated by reference in its entirety and in a manner consistent with the present invention.

The backsheet 12 may further comprise separate regions having different properties. In a preferred embodiment, portions of the backsheet 12 are air-permeable to improve the breathability of the garment 10. The different regions may be formed by making the backsheet 12 a composite of different sheet materials, chemical treatment, heat treatment, or other processes or methods known in the art. Some regions of the backsheet 12 may be fluid pervious. The backsheet 12 may also be made from a laminate of overlaid sheets of material or a composite of sheets joined to one another at or near their edges.

The substantially liquid-pervious topsheet 14 may comprise any suitable substantially liquid-pervious material currently known in the art or later discovered that permits passage of-at least liquids therethrough. Non-woven materials are exemplary because such materials readily allow the passage of liquids and other exudates to the underlying absorbent core 16. Examples of suitable topsheet materials include non-woven spun-bonded or carded webs of polypropylene, polyethylene, nylon, polyester, blends of these materials, and the like. The topsheet 14 may also be made of single-ply nonwoven material that may be made of carded fibers, either adhesively or thermally bonded, perforated plastic film, spunbonded fibers, or water entangled fibers that have a strength suitable for use as a topsheet material for the given application.

The topsheet 14 may further comprise several regions having different properties. In one embodiment, the portions of the topsheet 14 located away from the crotch region 26 are substantially fluid-impervious and hydrophobic. Different topsheet properties, such as fluid perviousness and hydrophobicity, may be imparted upon the topsheet 14 by treating the topsheet 14 with adhesives, surfactants, or other chemicals, using a composite of different materials, or by other means. The topsheet 14 may also be made from a lamninate of overlaid sheets of material or a composite of sheets joined to one another at or near their edges.

The backsheet 12 and the topsheet 14 preferably are "operatively associated" with one another. The term "operatively associated" or "associated," as understood in all contexts herein, encompasses all configurations whereby the location of one part is interrelated to the location of the part with which it is associated. For example, two parts may be associated with one another by directly joining them to one another, or by joining them to one another through an intermediary part. In addition, a part may be operatively associated with another part by being captured in place by surrounding parts, even though the captured part may not be physically attached to any other part.

Exemplary attachment methods for operatively associating the topsheet 14 with the backsheet 12 include the use of lines of hot melt adhesive, ultrasonic bonding, chemical bonding, stitching, and the like. While the backsheet 12 and topsheet 14 have substantially the same dimensions in the embodiments depicted herein, they may also have different dimensions. For example, in one embodiment the topsheet 14 may be substantially smaller than the backsheet 12, and may be just large enough to completely cover the absorbent core 16.

The garment may have any of a number of mechanical sealing devices to provide the garment 10 with a leak-proof fit around the wearer. In one embodiment, the garment 10 comprises leg gathers 30 disposed at or near the edge of each leg hole 20. Leg gathers 30 provide a gasketed, contracting fit around the wearer's legs, which may improve the leakage resistance of the garment 10. The leg gathers 30 may comprise one or more of several types of gather, including conventional leg gathers 30 (as shown) which are typically located very close to the edges of the leg holes 20, and standing leg gathers (not shown). Conventional leg gathers 30 are well known in the art, and are disclosed, for example, in U.S. Pat. No. 5,830,203, issued to Suzuki et al., which is incorporated herein by reference in its entirety, and in a manner consistent with the present invention. Standing leg gathers are also known in the art, and disclosed in U.S. Pat. No. 5,292,316, issued to Suzuki, which is incorporated herein by reference in its entirety, and in a manner consistent with the present invention.

Still referring to FIG. 1, fitting elastics 28 or other devices may be provided to hold the garment on the wearer. The fitting elastics 28 or other devices are selected to provide sufficient contracting force around the wearer's waist to hold the garment 10 on the wearer. The fitting elastics 28 or other devices may also provide leakage protection. In some cases, such as in the exemplary embodiments depicted herein, the fitting elastics 28 may be severed or gapped in places where the absorbent core 16 may extend into the waist region 24. Although the embodiments described herein all comprise fitting elastics 28, it should be understood that the present invention may not include fitting elastics 28. The present invention may also comprise any other mechanism or structure for holding the garment 10 on the wearer, such as openable side seams with adhesives or gripping tabs for fastening the garment around a wearer's waist.

The fitting elastics 28 preferably are operatively associated with the garment 10 in the waist region 24, and may also be associated with the garment 10 in the crotch region 26. The fitting elastics 28 may be operatively associated with the garment 10 by any of a variety of methods known in the art, such as ultrasonic bonding, adhesive bonding, chemical bonding, stitching, and the like. It is preferred that the fitting elastics 28 be disposed between the topsheet 14 and backsheet 12, however, they may be disposed on the exterior of either sheet, and may be covered by an additional sheet of material. During a preferred construction process, the fitting elastics 28 are stretched before being sandwiched and affixed between the topsheet 14 and backsheet 12, so that when the elastics contract, the waist region 24 contracts around the wearer's body.

In another embodiment, the fitting elastics 28 comprise a heat-activated elastic material, which is a material that becomes elastic when exposed to heat. Such a material may be sandwiched between the topsheet 14 and backsheet 12 in a relaxed state, and then heated to elasticize the waist region 24. Such materials and processes are disclosed in U.S. Pat. No. 4,640,859, issued to Hansen et al., the disclosure of which is incorporated herein by reference in its entirety.

The fitting elastics 28 may comprise strands or bands of any suitable elastic material, such as rubber, spandex, LYCRA, elastic polymers, and the like. Strands or bands of elastic typically provide elastic contraction only in the direction of their length, and thus may be referred to as directional elastics. The fitting elastics 28 also may comprise an elastic film, such as that disclosed in U.S. Pat. No. 6,159,584, issued to Eaton et al., which is herein incorporated by reference in its entirety, and in a manner consistent with the present invention. The fitting elastics 28 may also comprise a multidirectional elastic or elastic aggregate such as elastic foam materials, elastic webbing, netting, scrim elastic, such as FLEXCEL™ Elastic Nonwoven Laminate, available from Kimberly-Clark Corporation, headquartered in Neenah, Wisconsin, and the like. Elastics in the form of a film, foam, or multidirectional aggregate typically provide elastic contraction in all directions within the plane of the elastics, and may be referred to as multidirectional elastics.

In an embodiment of the invention in which the fitting elastics 28 comprise strands or bands of elastic material, the strands or bands may be oriented to form loops around the circumference of the waist region 24, or they may be provided at an angle to the circumference of the waist region 24. Fitting elastics 28, and other means of fitting absorbent garments to wearers, are generally known in the art. One skilled in the art will be able to design and manufacture appropriate fitting elastics 28 or other fitting devices that will hold the garment 10 on the wearer without undue experimentation.

Still referring to FIG. 1, an embodiment of the invention further comprises shaping elastics associated with the garment 10 in one or more target areas 32. For clarity, the shaping elastics are not individually shown, but are instead indicated by the target areas 32, which are shown as areas of diagonal lines.

The shaping elastics may comprise any suitable elastic material, such as those discussed herein with regard to the fitting elastics 28. The shaping elastics may also be provided in any suitable form, such as strands, scrim, foam, and the like, as described herein. The shaping elastics may also be associated with the garment 10 in any suitable manner, such as by adhesives, ultrasonic bonding, stitching, chemical bonding, or any other suitable method or combination of methods known in the art. The shaping elastics may be located on either side of the topsheet 14 or backsheet 12, or between them, and the garment 10 may comprise additional sheet layers to cover or hold the shaping elastics.

In an embodiment in which the garment 10 comprises fitting elastics 28 and the shaping elastics and fitting elastics 28 are both directional elastics, such as elastic strands or bands, the shaping elastics may be oriented in parallel with the fitting elastics 28 or at an angle to the fitting elastics 28. In another embodiment, one or both of the fitting elastics 28 and shaping elastics is a multidirectional elastic or elastic aggregate, as described above. In yet another embodiment, one or both of the fitting elastics 28 and shaping elastics comprises a combination of elastic materials or types. Other combinations of elastic materials, structures, locations, joining methods, and the like may also be used.

Conventional fitting elastics are designed to conform to the wearer's body to provide a high level of comfort and to allow the garment to follow the contours of the wearer's body throughout the wearer's range of motion. The shaping elastics of the present invention, on the other hand, are generally more rigid than conventional fitting elastics, and rather than the shaping elastics conforming to the wearer's body, the wearer's body generally conforms to the shape of the shaping elastics.

The shaping elastics provide additional contracting force to the garment 10 in the target areas 32, which makes the target areas 32 stiffer than other regions of the garment 10. The garment 10 may comprise one or more target areas 32, which may be located such that the additional contracting force provided by the shaping elastics provides body-shaping functions, such as firming up or reducing the body size, in various parts of the wearer's body. The target areas 32 may also be located to provide other benefits.

The stiffness of the shaping elastics in the target areas 32 may be designed to provide a greater or lesser amount of body shaping. A stiffer target area will tend to provide more of a shaping function, as it resists deformation caused by the wearer's body and instead forces the wearer's body to conform to garment in the target area 32, thus providing the desired body shape. The stiffness of the target area 32 may be increased or decreased in a variety of ways. One way to increase the stiffness the target area is to provide a greater density of shaping elastics per unit area of the target area 32. Another way to increase the stiffness of the target area 32 is to increase the spring constants of the shaping elastics, such as by providing a stiffer elastic material or increasing the cross-sectional dimensions of the shaping elastics. In one embodiment of the invention, the target areas 32 may be provided with the appropriate amount of stiffness by using a set of shaping elastics comprising the same material that is used for the fitting elastics 28. Such an embodiment may provide the added benefits of the invention at a relatively low cost. Selecting stiffer or less stiff arrangements of elastics is known in the art, and a skilled artisan will be able to provide the appropriate stiffness to the target areas 32 without undue experimentation, using the guidelines provided herein.

In the embodiment of FIG. 1, one target area 32 is located above each leg hole to provide additional support in the wearer's hips. In such an embodiment, the wearer may be provided with slimmer, firmer appearing hips.

Figure 2:
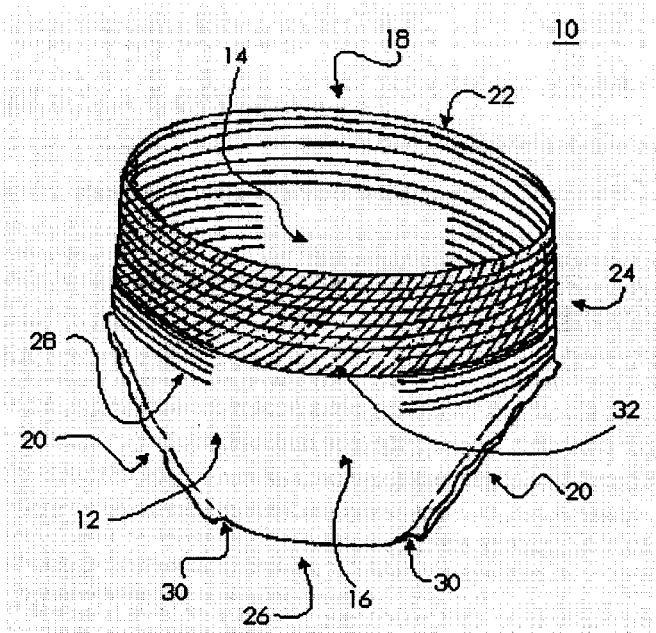
FIG. 2 is a view of an embodiment of the present invention, with shaping elastics disposed in the front half of the waist region.
Figure 3:
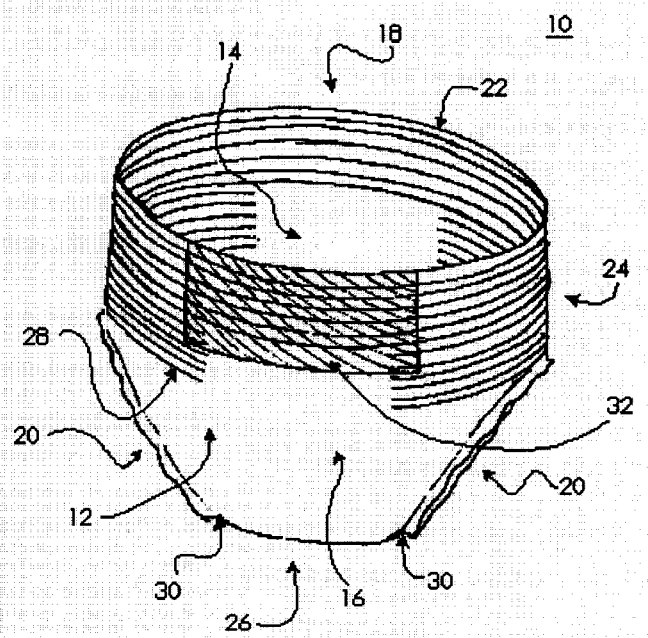
FIG. 3 is a view of an embodiment of the present invention, with shaping elastics disposed in the stomach portion of the waist region.

In another embodiment, depicted in FIG. 2, the garment comprises a target area 32 that extends across the entire front half of the waist region 24. Such an embodiment may help to flatten the front torso of a wearer, and may provide other benefits. In the embodiment of FIG. 3, a more localized target area 32 is provided in the waist region 24 adjacent to the wearer's stomach, to provide more localized body shaping.

Figure 4:
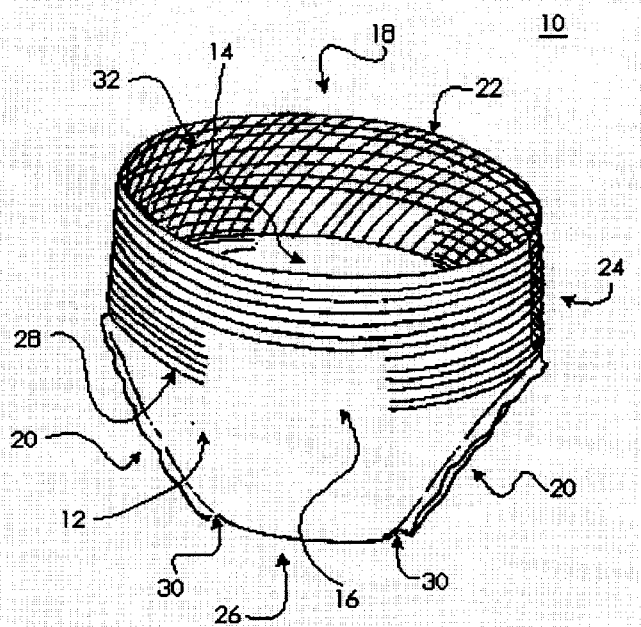
FIG. 4 is a view of an embodiment of the present invention, with shaping elastics disposed in the back half of the waist region.
Figure 5:
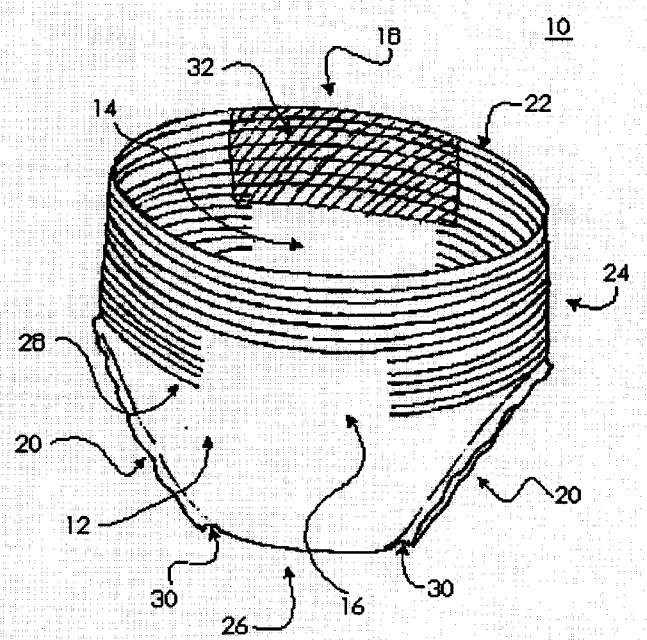
FIG. 5 is a view of an embodiment of the present invention, with shaping elastics disposed in the lower back portion of the waist region.

In another embodiment, depicted in FIG. 4, the garment comprises a target area 32 that extends across the entire back half of the waist region 24. Such an embodiment may provide physically therapeutic assistance or other benefits to the wearer. An embodiment may also comprise a more localized lower back-supporting target area 32, as depicted in FIG. 5.

Figure 6:
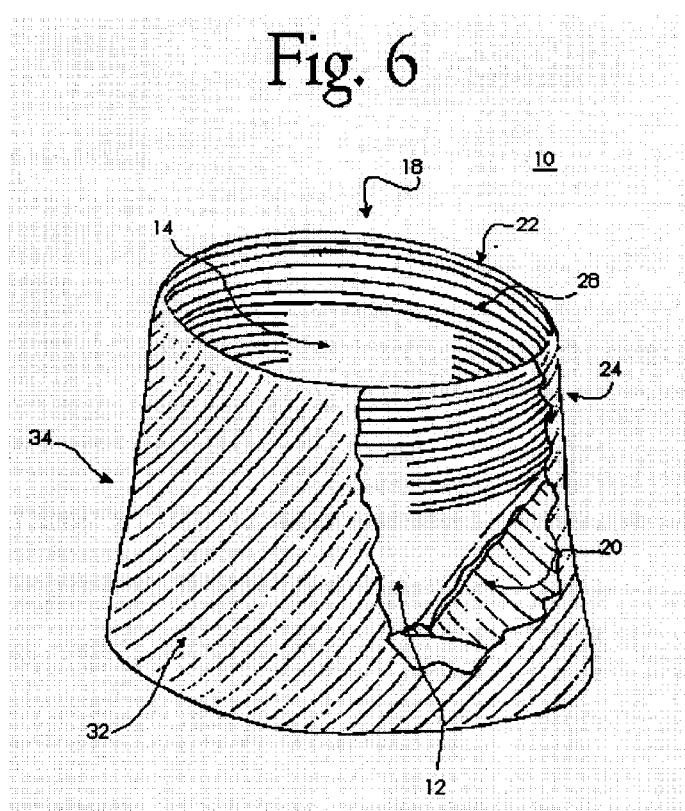
FIG. 6 is a cut away view of an embodiment of the present invention having an extended skirt-like structure, with the shaping elastics extending to encircle a wearer's waist, hips, and thighs.
Figure 7:
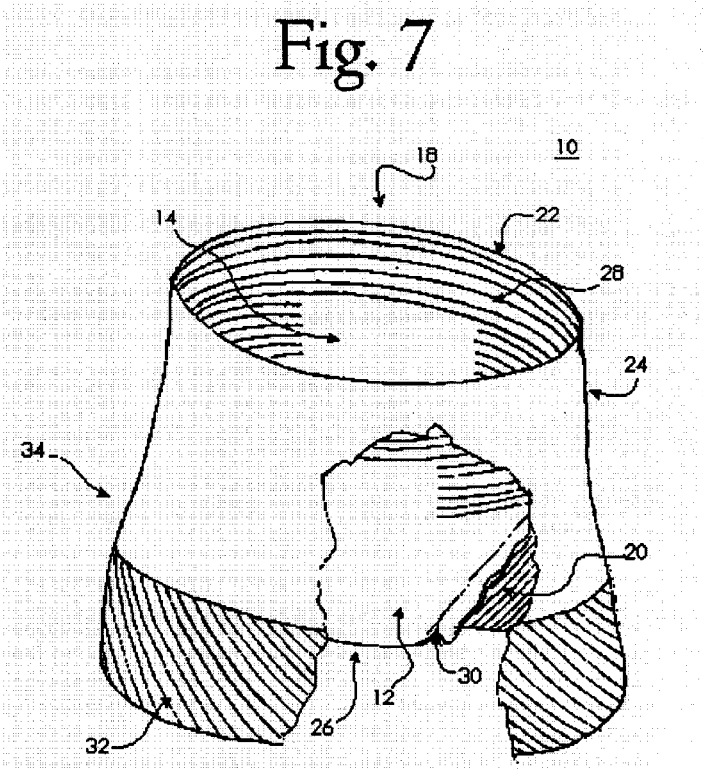
FIG. 7 is a cut away view of an embodiment of the present invention having an extended skirt-like structure, with the shaping elastics extending to encircle a wearer's and thighs.

In another embodiment, depicted in FIG. 6, the topsheet 14, backsheet 12, or both, may be extended upward from the waist edge 22, then doubled over to form a skirt-like structure 34 around the garment 10. The target area 32 may be located within the skirt-like structure 34. The target areas 32 in such an embodiment may be distributed throughout the entirety of the skirt-like structure 34 as shown in FIG. 6. In the embodiment of FIG. 6, the target area 32, and hence the shaping elastics, are located to completely encircle a wearer's thighs, hips, waist, and stomach to provide support and body shaping to those body parts. Alternatively, the target areas 32 may be located only in certain parts of the skirt-like structure 34, as is depicted in the embodiment in FIG. 7. In the embodiment of FIG. 7, the target areas 32 are located to encircle a wearer's thighs, but not other portions of a wearer's body. The garment 10 may also comprise several different target areas 32 in the skirt-like structure 34, each designed to provide different benefits to a different region of the wearer's body. In such an embodiment, a wearer may be able to adjust the target areas 32 to best benefit the wearer's particular body shape by adjusting the location of the skirt-like structure 34. For example a wearer of the embodiment of FIG. 7 may raise or lower the skirt like structure 34 to provide shaping to the wearer's thighs or hips.

Figure 8:
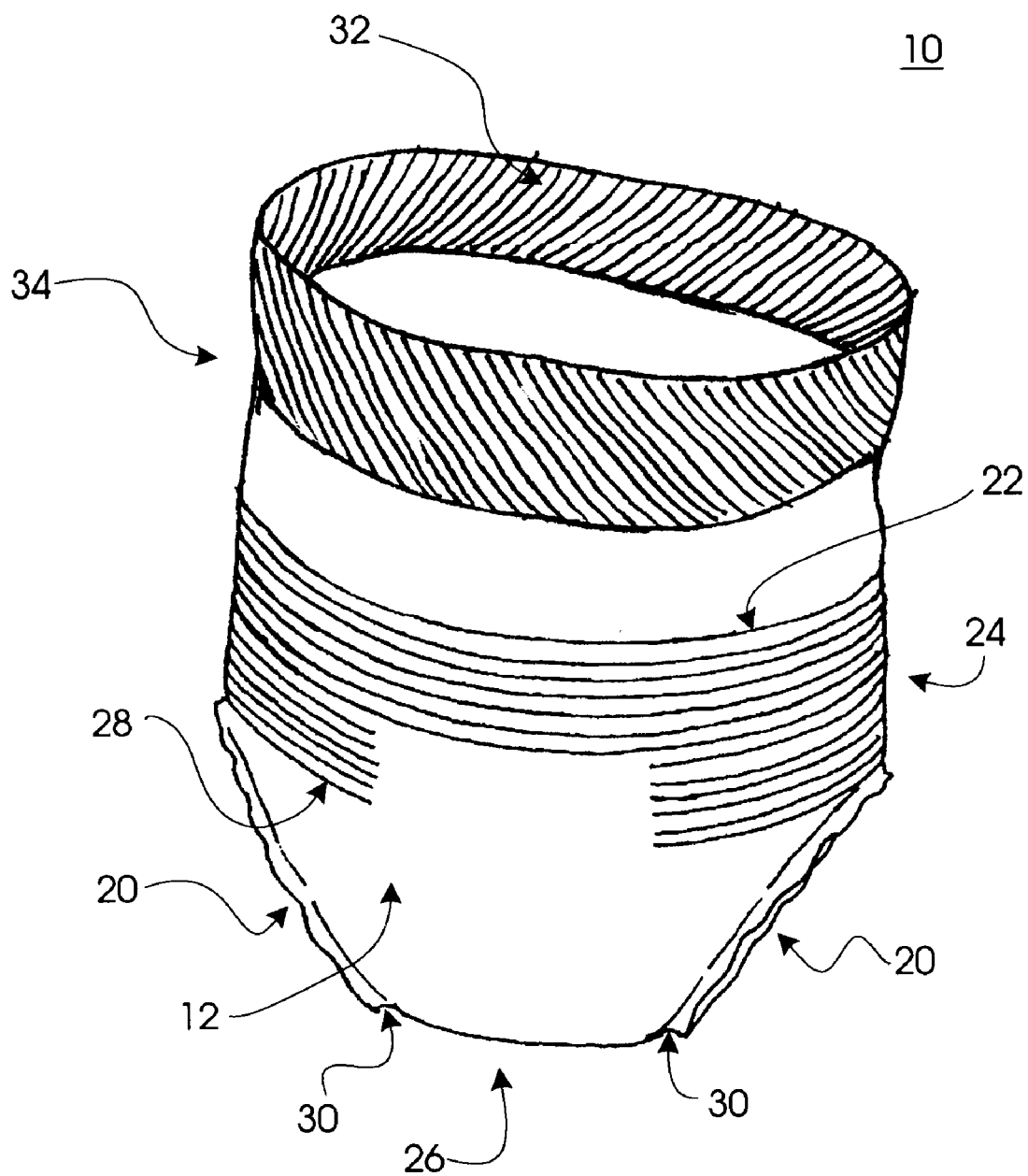
FIG. 8 is a view of an embodiment of the present invention having a corset-like structure, with the shaping elastics positioned to encircle a wearer's stomach.

Similarly, the skirt-like structure 34 may be inverted to wrap around the wearer's torso to provide a corset-like structure, in which the target areas 32, and hence the shaping elastics, may be located within the corset-like structure to provide body shaping to the wearer's torso. Such an embodiment is shown in FIG. 8.

The size of the target area or areas 32 in any embodiment may vary depending on factors such as: the size of the part of the body that is desired to be shaped, the amount of shaping desired, the desired comfort level, and other factors. The target areas 32 may extend from the waist edge 22 and extend all the way to the crotch region 26, leg holes 20, or both. The target areas 32 may also extend into the crotch region 26, or be offset from the waist edge 22.

In addition to providing beneficial body-shaping functions, the present invention may also be used to provide physically therapeutic body support. The added stiffness provided by the shaping elastics may also provide additional support to help the fitting elastics 28 or other fitting mechanism hold the garment on wearers that have body sizes that are between commercially available garment size ranges.

Such a garment may also provide additional comfort by preventing the garment 10 from "rolling" or "bunching." Rolling is a phenomenon in which the waist edge 22 curls over away from the wearer due to contact with the part of the wearer's body that lies just beyond the waist edge 22 of the garment 10 or contact with the wearer's clothing. The additional stiffness provided by the shaping elastics in the target areas 32 may help resist rolling. Bunching occurs when the garment 10 experiences forces that tend to compress the sheets comprising the garment 10 in the plane of the sheets, such as when the wearer's body or outer garments push down on the waist edge 22. Bunching may also occur when the wearer leans forward, sits down, or otherwise moves such that his or her body compresses and forms folds. The additional stiffness provided by the shaping elastics may resist the compressive forces that cause bunching, and may prevent the garment from following the contours of a wearer's folded skin so closely as to be uncomfortable.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. An absorbent garment comprising:
   a substantially liquid-impervious outer layer operatively associated with a substantially liquid-pervious inner layer to form a garment having a waist hole and a pair of leg holes;
   a waist edge defining the outer perimeter of the waist hole;
   a waist region at least partially encircling a wearer's waist proximal to the waist edge;
   a crotch region extending between the leg holes to at least partially extend between a wearer's legs;
   an absorbent layer disposed between the inner and outer layers in at least part of the crotch region, the absorbent layer being operatively associated with at least one of the inner and outer layers;
   one or more shaping elastics operatively associated with at least one of the inner and outer layers;
   a skirt structure formed by an extended region of at least one of the inner and outer layers and extending downward on a wearer from the waist edge, wherein the one or more shaping elastics are disposed at least partly within the skirt structure; and
   wherein the one or more shaping elastics reduce the apparent size of portions of a wearer's body.

2. The absorbent garment of claim 1, wherein the skirt structure is formed by an extended region of the outer layer.

3. The absorbent garment of claim 1, wherein the one or more shaping elastics comprise one or more directional elastics.

4. The absorbent garment of claim 1, wherein the one or more shaping elastics comprise one or more elastic aggregates.

5. The absorbent garment of claim 1, wherein the one or more shaping elastics comprise one or more elastic films.

6. The absorbent garment of claim 1, wherein the one or more shaping elastics comprise a heat-activated elastic material.

7. The absorbent garment of claim 1, wherein the one or more shaping elastics are distributed throughout the skirt structure.

8. An absorbent garment comprising:
   a substantially liquid-impervious outer layer operatively associated with a substantially liquid-pervious inner layer to form a garment having a waist hole and a pair of leg holes;
   a waist edge defining the outer perimeter of the waist hole;
   a waist region at least partially encircling a wearer's waist proximal to the waist edge;
   a crotch region extending between the leg holes to at least partially extend between a wearer's legs;
   an absorbent layer disposed between the inner and outer layers in at least part of the crotch region, the absorbent layer being operatively associated with at least one of the inner and outer layers;
   one or more shaping elastics operatively associated with at least one of the inner and outer layers;
   a corset structure formed by an extended region of at least one of the inner and outer layers and extending upward on a wearer from the waist edge, wherein the one or more shaping elastics are disposed at least partly within the corset structure; and
   wherein the one or more shaping elastics reduce the apparent size of portions of a wearer's body.

9. The absorbent garment of claim 8, wherein the corset structure is formed by an extended region of the outer layer.

10. The absorbent garment of claim 8, wherein the one or more shaping elastics comprise one or more directional elastics.

11. The absorbent garment of claim 8, herein the one or more shaping elastics comprise one or more elastic aggregates.

12. The absorbent garment of claim 8, wherein the one or more shaping elastics comprise one or more elastic films.

13. The absorbent garment of claim 8, wherein the one or more shaping elastics comprise a heat-activated elastic material.

14. The absorbent garment of claim 8, wherein the one or more shaping elastics are distributed throughout the corset structure.

* * * * *